US011166662B2

(12) United States Patent
Varpula et al.

(10) Patent No.: US 11,166,662 B2
(45) Date of Patent: Nov. 9, 2021

(54) MOBILE DEVICE FOR MEASURING ELECTRICAL BIOSIGNALS

(71) Applicant: VITALSIGNUM OY, Helsinki (FI)

(72) Inventors: Timo Varpula, Vantaa (FI); Panu Helistö, Espoo (FI)

(73) Assignee: VITALSIGNUM OY, Helsinki (FI)

( * ) Notice: Subject to any disclaimer, the term of this patent is extended or adjusted under 35 U.S.C. 154(b) by 97 days.

(21) Appl. No.: 16/084,728

(22) PCT Filed: Mar. 14, 2017

(86) PCT No.: PCT/FI2017/050168
§ 371 (c)(1),
(2) Date: Sep. 13, 2018

(87) PCT Pub. No.: WO2017/158237
PCT Pub. Date: Sep. 21, 2017

(65) Prior Publication Data
US 2019/0082987 A1 Mar. 21, 2019

(30) Foreign Application Priority Data
Mar. 15, 2016 (FI) ........................................ 20165214

(51) Int. Cl.
*A61B 5/389* (2021.01)
*A61B 5/0205* (2006.01)
(Continued)

(52) U.S. Cl.
CPC ............ *A61B 5/332* (2021.01); *A61B 5/0205* (2013.01); *A61B 5/02438* (2013.01); *A61B 5/30* (2021.01);
(Continued)

(58) Field of Classification Search
CPC . A61B 5/0404; A61B 5/04004; A61B 5/0205; A61B 5/02438
See application file for complete search history.

(56) References Cited

U.S. PATENT DOCUMENTS 5,713,939 A * 2/1998 Nedungadi ........ A61N 1/37211
607/29
9,295,403 B1 * 3/2016 Mirov .................. A61B 5/6824
(Continued)

FOREIGN PATENT DOCUMENTS

| GB | 2 075 194 | 11/1981 |
| GB | 2475091 | 5/2011 |
| WO | 2016/053731 | 4/2016 |

OTHER PUBLICATIONS

International Search Report for PCT/FI2017/050168, dated Jun. 8, 2017, 7 pages.
(Continued)

*Primary Examiner* — John R Downey
(74) *Attorney, Agent, or Firm* — Nixon & Vanderhye PC

(57) ABSTRACT

A mobile device for measuring at least one electrical biosignal. The device comprises a first input and a second input, a measuring circuit part for providing an output signal indicating the electrical biosignal to be measured, the measuring circuit part comprising a first input and a second input, and a charging circuit part for charging a rechargeable battery inserted in the device, the charging circuit part comprising a first input and a second input. The first input of the measuring circuit part and the first input of the charging circuit part are connected to the first input of the mobile device and the second input of the measuring circuit part and the second input of the charging circuit part are connected to the second input of the mobile device.

16 Claims, 3 Drawing Sheets

(51) Int. Cl.
*A61B 5/332* (2021.01)
*A61B 5/024* (2006.01)
*A61B 5/00* (2006.01)
*A61B 5/30* (2021.01)
*A61B 5/369* (2021.01)
*A61B 5/282* (2021.01)
*A61N 1/04* (2006.01)

(52) U.S. Cl.
CPC .............. *A61B 5/369* (2021.01); *A61B 5/389* (2021.01); *A61B 5/6804* (2013.01); *A61B 5/6831* (2013.01); *A61B 5/6833* (2013.01); *A61B 5/6898* (2013.01); *A61B 5/7225* (2013.01); *A61B 5/0002* (2013.01); *A61B 5/0006* (2013.01); *A61B 5/282* (2021.01); *A61B 2560/0209* (2013.01); *A61B 2560/0214* (2013.01); *A61B 2560/0443* (2013.01); *A61B 2560/0462* (2013.01); *A61B 2562/225* (2013.01); *A61N 1/0404* (2013.01)

(56) References Cited

U.S. PATENT DOCUMENTS

| | | | | |
|---|---|---|---|---|
| 2004/0077954 A1* | 4/2004 | Oakley | ................ | A61B 5/0006 600/483 |
| 2006/0222567 A1* | 10/2006 | Kloepfer | .............. | G01N 33/558 422/68.1 |
| 2013/0197348 A1* | 8/2013 | Stancer | ................ | A61N 1/3718 600/411 |
| 2014/0081100 A1* | 3/2014 | Muhsin | .................. | A61B 5/742 600/324 |
| 2014/0163355 A1* | 6/2014 | Kurpad | .................. | A61B 5/055 600/417 |
| 2015/0051670 A1* | 2/2015 | Hocken | ............... | A61N 1/36125 607/62 |
| 2015/0088221 A1* | 3/2015 | Barr-Cohen | ........... | A61N 1/362 607/33 |
| 2015/0113301 A1* | 4/2015 | Wang | .................... | G06F 1/3287 713/320 |
| 2015/0364018 A1* | 12/2015 | Mirov | ...................... | G08B 6/00 340/407.1 |
| 2015/0366506 A1* | 12/2015 | Chien | .................. | A61B 5/6833 600/392 |
| 2016/0022889 A1* | 1/2016 | Bluvshtein | .......... | A61M 1/1032 600/16 |
| 2016/0082272 A1* | 3/2016 | Karst | ...................... | H01L 31/12 607/61 |
| 2016/0114171 A1* | 4/2016 | Parker | ................ | A61N 1/36071 607/59 |
| 2016/0192857 A1* | 7/2016 | Lee | ..................... | A61B 5/02416 600/382 |
| 2017/0288451 A1* | 10/2017 | Trusty | ..................... | H04M 1/18 |

OTHER PUBLICATIONS

Written Opinion of the ISA for PCT/FI2017/050168, dated Jun. 8, 2017, 8 pages.
Search Report for FI20165214, dated Jun. 10, 2016, 1 page.

* cited by examiner

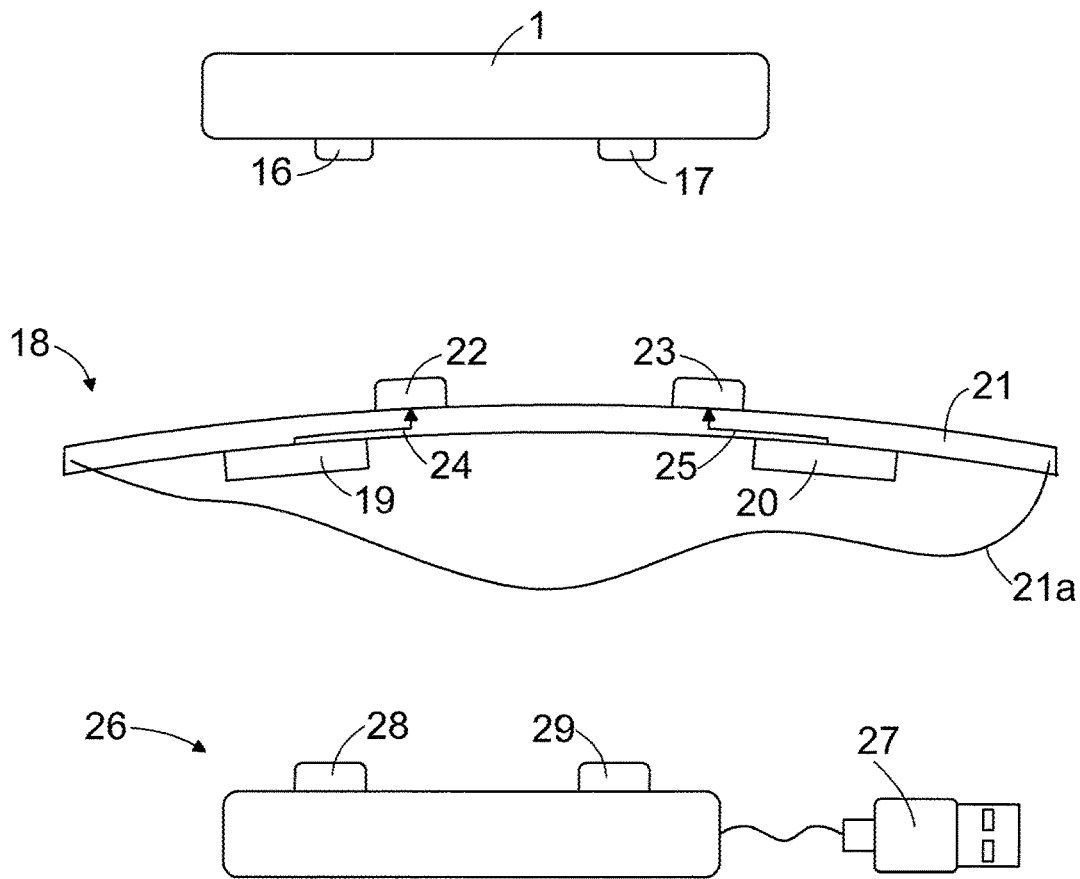
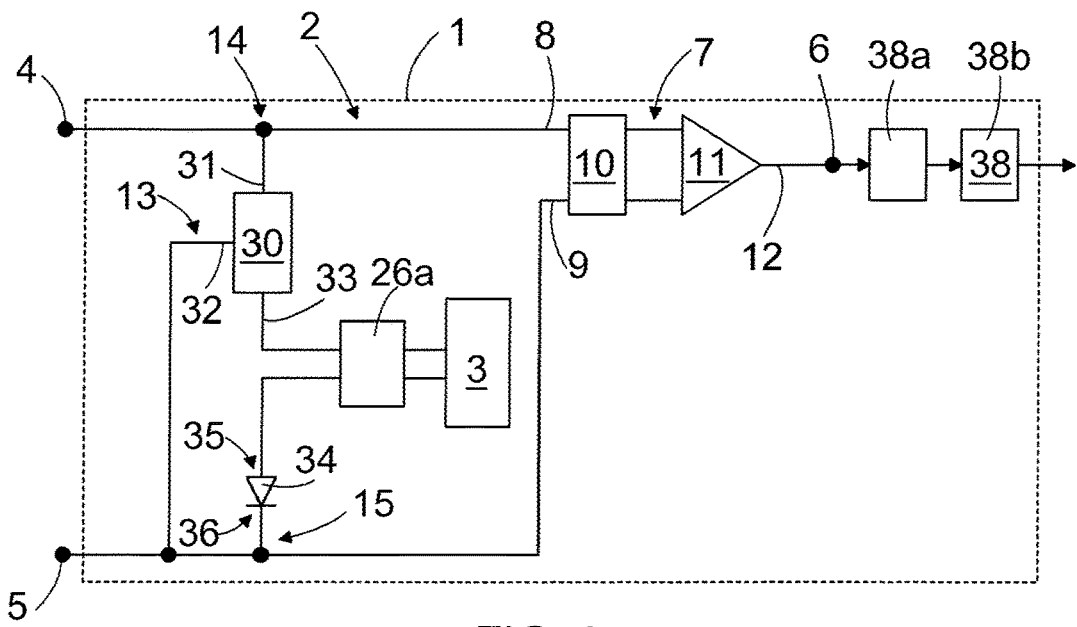

MOBILE DEVICE FOR MEASURING ELECTRICAL BIOSIGNALS

This application is the U.S. national phase of International Application No. PCT/FI2017/050168 filed 14 Mar. 2017 which designated the U.S. and claims priority to FI Patent Application No. 20165214 filed 15 Mar. 2016, the entire contents of each of which are hereby incorporated by reference.

FIELD OF THE INVENTION

The present invention relates to a mobile device for measuring at least one electrical biosignal.

BACKGROUND OF THE INVENTION

About 10% of population suffers from various cardiac problems such as arrhythmias, ischemia, heart attacks or palpitations. Atrial fibrillation is one of the most severe arrhythmias since it may cause strokes that may in turn lead to permanent neurological damage or death. Heart attack is the most common cause of death. Electrocardiogram (ECG) is the most powerful tool to monitor and diagnose the cardiac illnesses. Often the ECG is taken with a 24-72 hour recording using a mobile electrocardiogram device that is to be attached to a body of a person to be monitored with galvanic contact between the device electrodes and the user skin.

Heart rate monitoring devices are commonly used during physical training to optimize training level and to follow up condition development. Optical heart rate monitors based on photoplethysmography give indicative heart rate signal, but the most accurate heart rate reading is obtained from the R-peak of the ECG signal by using electrical heart rate monitors.

The mobile heart rate monitoring device or the mobile electrocardiogram device often has a rechargeable battery that is recharged through pins or a connector such as micro USB connector. In many devices a battery charger may be connected to the device while using the device. However, a faulty battery charger may then expose the user of the device to line voltages through the ECG contacts unless costly line isolation circuitry is used. Usage of the device during charging can also be prevented with a circuitry that detects if the device is connected to a charger and resets the microcontroller or powers down the electronics while connected to the charger. However, this alone does not prevent charging of the device while connected to human body.

BRIEF DESCRIPTION OF THE INVENTION

An object of the present invention is to provide a novel mobile device for measuring at least one electrical biosignal.

The invention is characterized by the features of the independent claims.

A mobile device for measuring at least one electrical biosignal comprises a first input and a second input, a measuring circuit part for providing an output signal indicating the electrical biosignal to be measured and comprising a first input and a second input as well as a charging circuit part for charging a rechargeable battery inserted in the device, the charging circuit part comprising a first input and a second input. Further in the mobile device the first input of the measuring circuit part and the first input of the charging circuit part are connected to the first input of the mobile device and the second input of the measuring circuit part and the second input of the charging circuit part are connected to the second input of the mobile device.

In the mobile device disclosed there are common inputs both for measuring the electrical biosignal to be measured and for recharging the battery of the mobile device. This means that charging of the battery of the mobile device may be easily prevented at the same time when the mobile device is in active operation and measuring the electrical biosignal of the user of the device, because either a measurement operation or a charging operation may be in use at a time. Thereby a possibly faulty battery charger device may not expose the user of the mobile device to line voltages through the measurement electrode contacts. The number of physical ports or contacts of the mobile device is also minimized, whereby system costs are reduced and immunity of the mobile device to humid or wet conditions is increased, since ports or contacts penetrating a device cover increase a risk to short circuits and failure to water leakages.

Some embodiments of the invention are disclosed in dependent claims.

In an embodiment an additional circuitry is used that detects if the device is connected to a charger and resets or powers down a microcontroller or a microprocessor of the device during recharging. This gives additional safety by preventing running of a measurement algorithm while the device is connected to the battery charger device. An additional benefit is that a reset action without additional pins or switches is provided in case normal operation of the microprocessor is for some reason disturbed during usage. Such reasons can be, e.g., electrical shocks, processor malfunction or firmware bugs that cause the algorithm to halt.

BRIEF DESCRIPTION OF THE DRAWINGS

In the following the invention will be described in greater detail by means of preferred embodiments with reference to the accompanying drawings, in which FIG. 1 shows schematically a side view of a mobile device for measuring at least one electrical biosignal, a wearable sensor module connectable to the mobile device and a battery charger device connectable to the mobile device;

FIG. 2 shows schematically an internal circuit diagram of the mobile device of Figure;

For the sake of clarity, the figures show some embodiments of the invention in a simplified manner. Like reference numerals identify like elements in the figures.

DETAILED DESCRIPTION OF THE INVENTION

Figure 3:
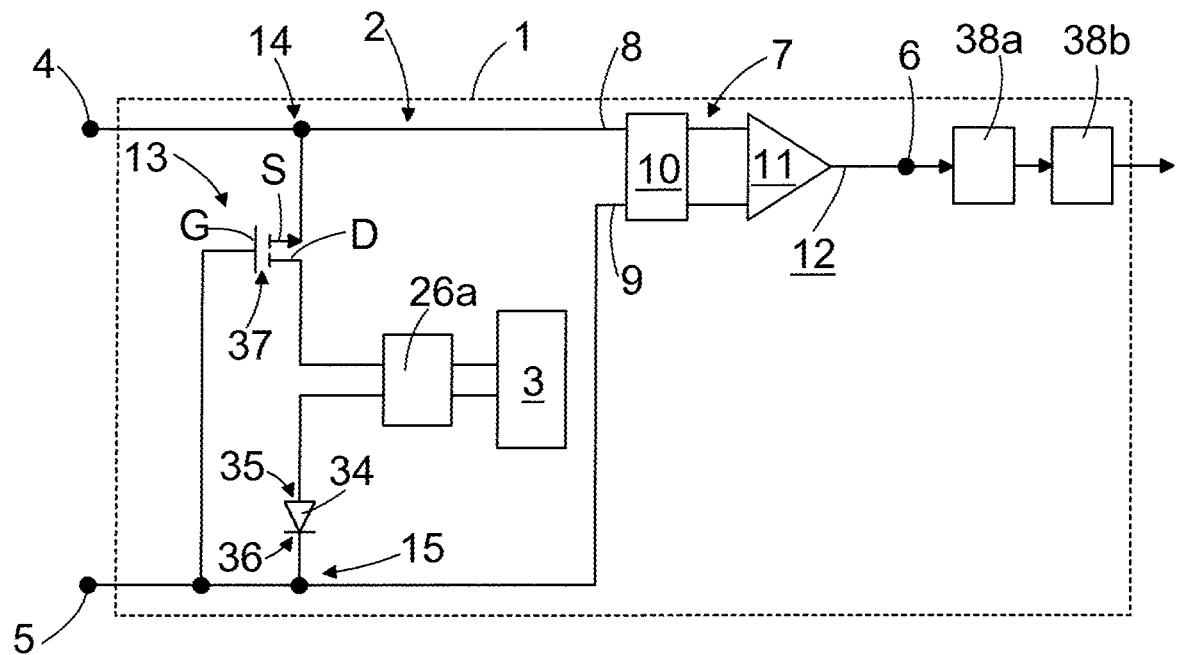
FIG. 3 shows schematically an embodiment of the internal circuit diagram of FIG. 2.

FIG. 1 shows schematically a side view of a mobile device 1 for measuring at least one electrical biosignal. FIG. 1 further shows a side view of a wearable sensor module 18 connectable to the mobile device 1 and collecting a signal that describes the electrical biosignal to be measured, as well as a side view of a battery charger device 26 connectable to the mobile device 1 for recharging a rechargeable battery inserted in the mobile device 1.

The mobile device 1 may for example be a heart rate monitor for measuring a heart rate of a user of the device 1, in which case the electrical biosignal to be measured describes the heart rate of the user of the device 1. Alternatively the mobile device 1 may be a mobile electrocardiogram device for measuring an electrocardiogram (EKG) of the user of the device 1, in which case the electrical biosignal to be measured describes the electrical activity of the heart of the user of the device 1. Alternatively the mobile device 1 may be a mobile electromyogram device for measuring an electromyogram (EMG) of the user of the device 1, in which case the electrical biosignal to be measured describes the electrical activity of muscles of the user of the device 1. Alternatively the mobile device 1 may be a mobile electroencephalogram device for measuring an electroencephalogram (EEG) of the user of the device 1, in which case the electrical biosignal to be measured describes the electrical activity of the brain of the user of the device 1. In addition, the mobile device may detect any electrical functions of the body, for example the electrical activity of organs such as eye, stomach, liver etc. The mobile device may also be used for measuring the electrical properties of the body, e.g. the bioimpedance of the body. The signals describing the electrical activities of the organs or the electrical properties of the body are also electrical biosignals that may be measured with the device 1.

It is also possible to use the device, instead of measuring a biosignal, to drive an electrical signal to the body to activate the neural or muscular system, through, e.g., transcutaneous electrical nerve stimulation—TENS, functional electrical stimulation—FES, or electrical muscle stimulation—EMS.

Alternatively to the devices and the electrical biosignals to be measured as listed above, the mobile device 1 may be intended to measure some other electrical biosignal or electrical properties of the user of the device 1. In the following description disclosing some embodiments of the mobile device 1, it is assumed that the mobile device 1 is intended to measure the electrocardiogram (EKG) of the user of the device 1.

FIG. 2 shows schematically an embodiment of an internal circuit 2 of the mobile device 1. In FIG. 2 the mobile device 1 is shown very schematically by a box drawn with a broken line. The mobile device 1 comprises a rechargeable battery 3 for providing an operating power of the mobile device 1. The rechargeable battery 3 may be replaceable because of a failure of the battery 3 or because of a reduced operating capability of the battery 3. The battery 3 may also be replaced after a certain predetermined lifetime of the battery 3 has passed. The battery 3 may for example be a lithium ion battery.

The internal circuit 2 comprises a first input 4 being a first input 4 of the mobile device 1. In the embodiments disclosed the first input 4 is a positive input 4. The voltage level in the first input 4 may be five volts when a battery charger device 26 is connected to the mobile device 1, for example. The internal circuit 2 comprises also a second input 5 being a second input 5 of the mobile device 1. In the embodiments disclosed the second input 5 is a negative input 5 or a lower voltage level input 5, i.e. an input connected to a lower voltage level in the mobile device 1. The second input 5 may thus be grounded, in which case the voltage level in the second input 5 is zero volt. Alternatively the second input 5 may be a virtual ground input having a voltage level less than the voltage level in the first input 4. According to an embodiment the voltage level in the second input 5 is 1-4 volts for example.

The internal circuit 2 further comprises a measurement signal output 6, through which a measurement signal indicating the electrical biosignal to be measured is supplied to an analog-to-digital converter and via a radio communication circuitry out of the mobile device 1 for further analysis and/or representation. The analog-to-digital converter is shown schematically with a box denoted with a reference sign 38a and the radio communication circuitry is shown schematically with a box denoted with a reference sign 38b.

The internal circuit 2 comprises a measuring circuit part 7 for retrieving the signal indicating the electrical biosignal to be measured. The measurement signal describing the electrical biosignal to be measured is connected by the wearable sensor module 18 which is attached to the user of the device 1 to the mobile device 1 as described later in more detail. The measuring circuit part 7 comprises a first input 8 and a second input 9. The first input 8 of the measuring circuit part 7 is connected to the first input 4 of the mobile device 1, and the second input 9 of the measuring circuit part 7 is connected to the second input 5 of the mobile device 1. The measuring circuit part 7 thus receives through the inputs 4, 5 of the internal circuit 2 an electrical signal from the wearable sensor module 18 connected to the mobile device 1, which electrical signal contains, possibly together with many other unrelated signals and measurement noise, a signal portion that describes the electrical biosignal to be measured.

The measuring circuit part 7 of FIGS. 2 and 3 comprises a measurement filter 10 and an amplifier 11 connected in series with the measurement filter 10. The measurement filter 10 is a circuit that retrieves the signal portion, i.e. in a case of the electrocardiogram measurement the electrocardiogram signal, actually describing or indicating only the electrical biosignal from the measurement signal received from the wearable sensor module 18 through the inputs 4, 5 of the internal circuit 3, which measurement signal may also contain noise or other unrelated signal portions. The amplifier 11 amplifies the signal retrieved by the measurement filter 10 for an analog-to-digital conversion and to a transmission of the retrieved signal out of the mobile device 1. The digital signal may be transmitted out of the mobile device 1 via a wired transmission but preferably wirelessly using local area network or Bluetooth radio.

The configuration of the measuring circuit part 7 may vary from that disclosed in FIGS. 2 and 3 depending on the electrical biosignal to be measured, for example.

The internal circuit 2 of the mobile device 1 also comprises a charging circuit part 13 having parts 26a, 30 and 34 for recharging the rechargeable battery 3 of the mobile device 1. According to an embodiment, part 26a is a battery charging chip, e.g. MAX1555, part 30 is a switching element that may be a mechanical or solid-state switch but preferably a P-channel MOSFET transistor, part 34 is a diode. The charging circuit part 7 comprises a first input 14 and a second input 15.

The first input 14 of the charging circuit part 13 is connected to the first input 4 of the mobile device 1, and the second input 15 of the charging circuit part 13 is connected to the second input 5 of the mobile device 1. The charging circuit part 13 receives through the inputs 4, 5 of the internal circuit 2 charging current from the battery charger device 26 connectable to the mobile device 1.

In the mobile device 1 disclosed above the first input 8 of the measuring circuit part 7 and the first input 14 of the charging circuit part 13 are both connected to the first input 4 of the mobile device 1, and the second input 9 of the measuring circuit part 7 and the second input 15 of the charging circuit part 13 are connected to the same second input 5 of the mobile device 1. To be more precise, in the embodiments disclosed the first input 14 of the charging circuit part 13 is combined with the first input 8 of the measuring circuit part 7, that are connected together to the first input 4 of the mobile device 1, and the second input 15 of the charging circuit part 13 is combined with the second input 9 of the measuring circuit part 7, that are connected together to the first input 4 of the mobile device 1.

Alternatively, the first input 8 of the measuring circuit part 7 and the first input 14 of the charging circuit part 13 could be connected through separate lines to the first input 4 of the mobile device 1 and the second input 9 of the measuring circuit part 7 and the second input 15 of the charging circuit part 13 could also be connected through separate lines to the second input 5 of the mobile device 1.

In other words, the mobile device 1 disclosed above comprises common inputs both for measuring the electrical biosignal to be measured and for recharging the battery 3 of the mobile device 1.

For actually connecting the mobile device 1 to the wearable sensor module 18 and to the battery charger device 26 the mobile device 1 comprises a first connector element 16 connected to the first input 4 of the internal circuit 2 and a second connector element 17 connected to the second input 5 of the internal circuit 2 of the mobile device 1. The first 16 and the second 17 connector elements in the device 1 connect the device 1 both mechanically and electrically to the wearable sensor module 18 and the battery charger device 26 through counterpart connector elements in the wearable sensor module 18 and the battery charger device 26. The wearable sensor module 18 and the battery charger device 26 are described shortly next with reference to FIG. 1.

The wearable sensor module 18 comprises a first measuring electrode 19 and a second measuring electrode 20 that are brought into contact with a skin of the user of the mobile device 1. The wearable sensor module 18 of FIG. 1 comprises a strap 21 to which the measuring electrodes 19, 20 are attached to, and the strap 21 is to be put around a body of the user of the mobile device 1 by using a band 21*a*. Instead of the strap 21 a shirt, a cap or other piece of clothing could also provide a foundation for the measuring electrodes 19, 20. The wearable sensor module 18 further comprises a first connector element 22 to which the first measuring electrode 19 is connected through a first signal line 24 and a second connector element 23 to which the second measuring electrode 20 is connected through a second signal line 25.

When the mobile device 1 is taken in use, the first connector element 16 of the mobile device 1 is connected to the first connector element 22 in the wearable sensor module 18 and the second connector element 17 of the mobile device 1 is connected to the second connector element 23 in the wearable sensor module 18. The connection between the connector elements 16, 17 in the mobile device 1 and the connector elements 22, 23 in the wearable sensor module 18 provide both the mechanical and the electrical connection between the mobile device 1 and the wearable sensor module 18. After that the wearable sensor module 18 is put on the user of the mobile device 1 in such a way that the measuring electrodes 19, 20 of the wearable sensor module 18 are brought into contact with the skin of the user of the mobile device 1 and the mobile device 1 is turned on.

The battery charger device 26 comprises a plug 27 through which the battery charger device 26 may be connected to a power supply for recharging the battery 3 in the mobile device 1. In the embodiment of the battery charger device 26 of FIG. 1 the plug 27 is a USB-port plug which may be connected to a USB-port in a portable computer, for example. Other kind of battery charger devices, like the ones comprising a voltage transformer, may also be applied. The battery charger device 26 further comprises a first connector element 28 and a second connector element 29 through which the battery charger device 26 may be connected to the mobile device 1.

When the battery 3 of the mobile device 1 is to be recharged, the mobile device 1 is unfastened from the wearable sensor module 18 and the first connector element 16 of the mobile device 1 is connected to the first connector element 28 of the battery charger device 26 and the second connector element 17 of the mobile device 1 is connected to the second connector element 29 of the battery charger device 26. The connection between the connector elements 16, 17 in the mobile device 1 and the connector elements 28, 29 in the battery charger device 26 provide both the mechanical and the electrical connection between the mobile device 1 and the battery charger device 26. After the battery 3 of the mobile device 1 is recharged, the mobile device 1 is unfastened from the battery charger device 26 and the mobile device 1 may be started to use again.

As stated above, the mobile device 1 disclosed comprises common inputs both for measuring the signal describing or containing a signal indicating the electrical biosignal to be measured and for recharging the battery of the mobile device.

This means firstly, that charging of the mobile device 1 may be easily prevented at the same time when the mobile device 1 is connected to the wearable sensor module 18, i.e. the charging of the mobile device 1 is prevented at the same time when the mobile device 1 is in operation and measuring the electrical biosignal of the user of the device 1, because either a measurement operation or a charging operation may be in use at a time. Thereby a possibly faulty battery charger device may not expose the user of the mobile device 1 to line voltages through the measurement electrode contacts.

Secondly, the number of physical ports or contacts of the mobile device 1 is also minimized, whereby system costs are reduced. Also the immunity of the mobile device 1 to humid or wet conditions, for example due to sweating, swimming or shower, is increased, since ports or contacts penetrating a device cover increase a risk to short circuits and failure to water leakages.

As stated above, the connector elements 16, 17 in the mobile device 1 and the connector elements 22, 23 in the wearable sensor module 18 or the connector elements 28, 29 in the battery charger device 26 provide both the mechanical and the electrical connection between the mobile device 1 and the wearable sensor module 18 or the battery charger device 26. That kind of connection may be implemented for example with snap fasteners. The connector elements 16 and 17 can also be part of a single electromechanical connector that snaps on a receptacle connector in the wearable sensor module 18 and the battery charger device 26. The connectors in mobile device 1 and the wearable sensor module 18 can have a multitude of other connector elements for connecting to other sensor elements in the wearable sensor module 18, e.g. to other ECG electrodes or to a temperature sensor. The connector elements 28 and 29 may likewise be incorporated in a single connector to which the connector in mobile device 1 is attached.

Referring to FIG. 2 again, the charging circuit part 13 of the mobile device 1 comprises a switching element 30 that is connected both to the first signal input 4 of the mobile device 1 and to the second signal input 5 of the mobile device 1. The switching element 30 detects a presence of the battery charger device 26 whereby the switching element 30 is configured to switch the charging circuit part 13 on a low-impedance on-state for charging the battery 3 of the mobile device 1. When the battery charger device 26 is removed from the mobile device 1, the switching element 30 is configured to switch the charging circuit part 13 back to a high-impedance off-state for the measurement of the at least one electrical biosignal.

The switching element 30 of FIG. 2 comprises a first connection 31 that is connected to the first input 4 of the mobile device 1. The switching element 30 comprises a second connection 32 that is connected to the second input 5 of the mobile device 1. The switching element 30 of FIG. 2 comprises also a third connection 33 that is to be connected to the battery charging chip 26a in the circuit 2 of the mobile device 1.

The charging circuit part 13 comprises also the diode 34. The diode 34 comprises a first connection 35, i.e. an anode connection that is to be connected to the battery charging chip 26a. The diode 34 comprises also a second connection 36, i.e. a cathode connection that is connected to the second input 5 of the mobile device 1. The diode 34 prevents any possible current flow from the direction of the second input 5 of the mobile device 1 towards the first input 4 of the mobile device 1 in a case that the second input 5 is not a completely grounded input but a virtual ground input having a voltage level above zero volts.

When the battery charger device 26 is connected to the mobile device 1, the battery charger device 26 will thus be connected between the switching element 30 and the diode 34 in the charging circuit part 13, whereby the switching element 34 activates and allows a charging current flow in the charging circuit part 13 and the battery 3 is started to be recharged. When the battery charger device 26 is disconnected from the mobile device 1, the switching element 30 deactivates and a current flow in the charging circuit part 13 is prevented. The switching element 30 thus provides a kind of a detection circuit which automatically detects whether a battery charger device 26 is connected to the mobile device 1 or not and correspondingly either allows or disallows a current flow in the charging circuit part 13.

According to an embodiment the switching element 30 is a transistor 37, such as a field effect transistor or a FET transistor. The switching element 30 could also be a transistor pair, such as a complementary CMOS transistor pair. FIG. 3 shows schematically an embodiment of the internal circuit 2 of FIG. 2 when the switching element 34 is a single transistor 37.

In the embodiment of FIG. 3, a source S of the transistor 37 provides the first connection 31 of the switching element 30 that is connected to the first input 4 of the mobile device 1. A gate G of the transistor 37 provides the second connection 32 of the switching element 30 that is connected to the second input 5 of the mobile device 1. A drain D of the transistor 37 provides the third connection 33 of the switching element 30 that is to be connected to the battery charging chip 26a when the battery charger device 26 is connected to the mobile device 1.

When the battery charger device 26 is connected to the mobile device 1 the transistor 37 switches to the low-impedance on-state for allowing a current flow in the charging circuit part 13. When the battery charger device 26 is disconnected from the mobile device 1 the transistor 3 switches back to the high-impedance off-state for preventing the current flow in the charging circuit part 13.

When the switching element 30 is implemented by a transistor 37, the switching element 30 has a very simple and cost-efficient implementation. Other kinds of switching element embodiments different from those disclosed above are naturally possible.

Switching element may be a mechanical or solid-state relay controlled by a microprocessor of the mobile device 1. In this embodiment, the input of a voltage comparator is connected to the input 4 of the mobile device 1. The output of the voltage comparator is given to the microprocessor. When the battery charger device 26 is connected to the mobile device 1, the voltage comparator detects that the input 4 of the mobile device 1 is at a high charging voltage and supplies a signal to the processor that closes the switching element 30 and a charging current flows onto the battery charging chip 26a. When the mobile device 1 is measuring the electrical biosignal, the voltage comparator detects that the voltage level of the input 4 of the mobile device 1 is low and thereby the processor opens the switching element 30.

Figure 4:
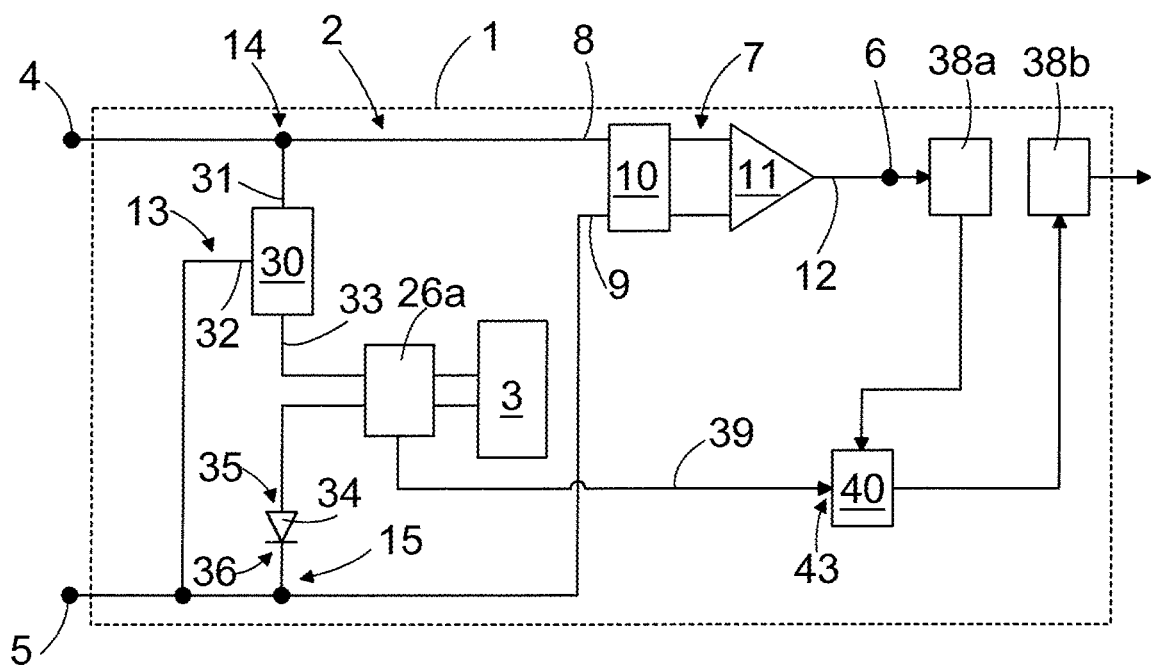
FIG. 4 shows schematically a second internal circuit diagram of the mobile device.
Figure 5:
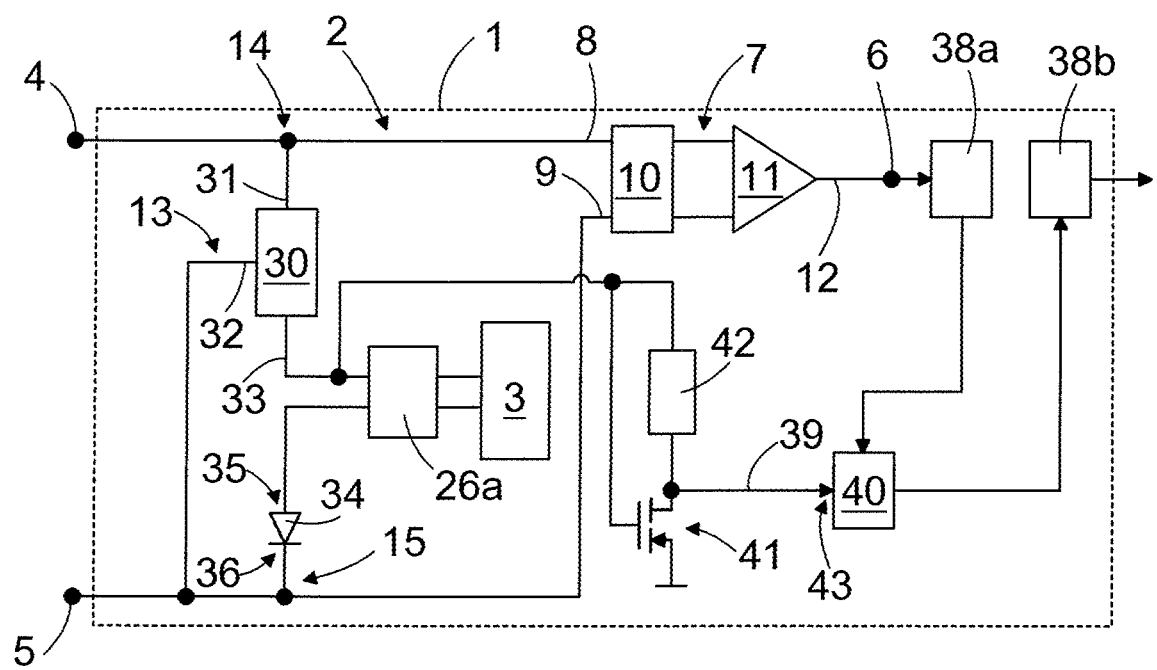
FIG. 5 shows schematically an embodiment of the internal circuit diagram of FIG. 4.

In the embodiment of FIG. 4, the battery charging circuitry 13 and/or the battery charging chip 26a provides an additional reset signal 39 when device 1 is connected to the battery charger device 26. The signal 39 is used to stop normal operation of the device 1 by resetting a microcontroller 40 or a microprocessor 40 which runs or executes the firmware responsible for controlling operations in the mobile device 1. A simple realization of such resetting circuitry is shown in FIG. 5. A MOSFET transistor 41 detects whether signal in the third connection 33 of the switching element 30 in the battery charging circuitry is ON and goes to LOW-state. A resistor 42 serves as a pull-up resistor. The reset signal output 39 of the transistor 41 is taken to the reset input 43 of the microcontroller 40. In this way operation of the device 1 is prevented while connected to battery charger device 26 providing charging current. An additional benefit is that the microcontroller 40 can be reset without additional switches or output pins penetrating the device 1 cover in case the normal operation of the device 1 is halted due to malfunction of the microcontroller.

It will be obvious to a person skilled in the art that, as the technology advances, the inventive concept can be implemented in various ways. The invention and its embodiments are not limited to the examples described above but may vary within the scope of the claims.

The invention claimed is:

1. A mobile device for measuring at least one electrical biosignal, the mobile device comprising:
    a measuring circuit configured to provide an output signal indicating the electrical biosignal to be measured, the measuring circuit comprising a first input and a second input,
    a charging circuit configured to charge a rechargeable battery inserted in the device, the charging circuit comprising a first input and a second input,
    a microcontroller configured to execute firmware configured to control operations in the mobile device, the charging circuit being further configured to provide a reset signal the state of which is arranged to change when the mobile device is connected to a battery charger, the reset signal being used to power down and restart the microcontroller, wherein:
    the mobile device further comprises a first input and a second input, and
    the first input of the charging circuit is combined with the first input of the measuring circuit, the first input of the measuring circuit and the first input of the charging circuit being connected to the first input of the mobile device, the second input of the charging circuit is combined with the second input of the measuring circuit, the second input of the measuring circuit and the second input of the charging circuit being connected to the second input of the mobile device, and the charging circuit comprises a switching element configured to switch the charging circuit to a low-impedance on-state for charging the rechargeable battery inserted in the mobile device and to a high-impedance off-state for the measurement of the at least one electrical biosignal.

2. The mobile device as claimed in claim 1, wherein the measuring circuit comprises a measurement filter for retrieving an output signal indicating the electrical biosignal to be measured and an amplifier configured to amplify the retrieved signal indicating the electrical biosignal to be measured.

3. The mobile device as claimed in claim 1, wherein the switching element is a transistor, wherein a source of the transistor is connected to the first input of the mobile device, a gate of the transistor is connected to the second input of the mobile device, and a drain of the transistor is connectable to a current supply for charging the rechargeable battery, the transistor switching to the low-impedance on-state in response to the current supply being connected to the mobile device.

4. The mobile device as claimed in claim 1, wherein
the mobile device further comprises a first connector element connected to the first input of the mobile device and a second connector element connected to the second input of the mobile device, the first connector element and the second connector element being configured to provide both a mechanical and an electrical connection between the mobile device and a wearable sensor module or a battery charger connectable to the mobile device.

5. The mobile device as claimed in claim 1, wherein the reset signal is generated in connection with an element configured to sense a state of a signal that is arranged to activate in response to the battery charger being connected to the mobile device to in turn activate the reset signal to power down and restart the microcontroller.

6. The mobile device as claimed in claim 5, wherein the element is a MOSFET transistor.

7. The mobile device as claimed in claim 1, wherein the mobile device is a heart rate monitor for measuring a heart rate, an electrocardiogram device for measuring an electrocardiogram, an electromyogram device for measuring an electromyogram, and/or an electroencephalogram device for measuring an electroencephalogram.

8. The mobile device as claimed in claim 1, wherein the reset signal is used to power down and restart the microcontroller, including stopping the microcontroller.

9. The mobile device as claimed in claim 1, wherein the reset signal is provided by a transistor connected to a third connector element of the switching element and a pull-up resistor connected to the transistor.

10. The mobile device as claimed in claim 9, wherein the transistor is configured to indicate whether a signal in the third connector element of the switching element in the battery charging circuit is ON and goes to a LOW state.

11. The mobile device as claimed in claim 10, wherein, based on the reset signal provided by the transistor, operation of the device is prevented while the device is connected to a battery charger providing charger current.

12. The mobile device as claimed in claim 10, wherein the microcontroller is resettable to power down and restart as a result of the reset signal, without additional switches or output pins penetrating a cover of the device in a case where normal operation of the device is halted because of a malfunction of the microcontroller.

13. A kit comprising a wearable sensor module and the mobile device as claimed in claim 1, the wearable sensor module being connectable to the mobile device and comprising:
at least one pair of measurement electrodes for measuring a signal describing at least one electrical biosignal to be measured, and
a first connector element and a second connector element connectable to the first and the second connector elements of the mobile device for connecting the wearable sensor module both mechanically and electrically to the mobile device.

14. A kit comprising a battery charger and the mobile device as claimed in claim 1, the battery charger being connectable to the mobile device and comprising:
a first connector element and a second connector element connectable to the first and the second connector elements of the mobile device for connecting the battery charger both mechanically and electrically to the mobile device.

15. A method of using the mobile device as claimed in claim 1 to drive an electrical signal to a body of a user of the device to activate a neural or muscular system.

16. A method of using the mobile device as claimed in claim 1 to drive an electrical signal to a body of a user of the device to measure electrical properties.

* * * * *